United States Patent [19]

Doherty et al.

[11] Patent Number: 4,540,000

[45] Date of Patent: Sep. 10, 1985

[54] SIGNAL CONDITIONER FOR BIOLOGICAL SIGNALS

[75] Inventors: Richard F. Doherty, Seaford; Anthony Pierry, Bayshore, both of N.Y.

[73] Assignee: OCG Technology Inc., New York, N.Y.

[21] Appl. No.: 561,810

[22] Filed: Dec. 15, 1983

[51] Int. Cl.$^3$ .............................................. A61B 5/04
[52] U.S. Cl. ...................................................... 128/696
[58] Field of Search ................ 128/695, 696, 702–706, 128/708, 710, 901, 902

[56] References Cited

U.S. PATENT DOCUMENTS

| | | | |
|---|---|---|---|
| 3,580,243 | 5/1971 | Johnson | 128/902 |
| 3,699,948 | 10/1972 | Ota et al. | 128/710 |
| 3,939,824 | 2/1976 | Arneson et al. | 128/901 |
| 4,034,745 | 7/1977 | Bloom | 128/706 |
| 4,240,442 | 12/1980 | Andresen et al. | 128/708 |
| 4,325,384 | 4/1982 | Blaser et al. | 128/902 |

Primary Examiner—William E. Kamm

Attorney, Agent, or Firm—Jacobs & Jacobs

[57] ABSTRACT

A signal conditioner for use with cardiographic data and other biological signals includes a baseline shift circuit and a variable gain amplifier. A feedback loop is provided for the output signal with a reference which designates the maximum value of the output signal. Within the baseline shifting circuit, there is provided circuitry which compares the amount of offset of the negative excursions of the waveform from a reference lead so as to introduce a feedback compensation signal which shifts the baseline and thereby compensates for drift in the baseline. Integration circuitry in the form of counters of clock pulses are provided in the control of both amplifier gain and baseline shift. Timing circuitry provides for the interleaving of set-up intervals with data aquisition intervals, the gain adjustment and baseline adjustment being accomplished only during the set-up intervals. Sensing of temporal data by waveform analysis is utilized for restarting the timing sequence whenever the format of the sensed biological signal falls outside of the predetermined limits.

15 Claims, 7 Drawing Figures

SIGNAL CONDITIONER FOR BIOLOGICAL SIGNALS

BACKGROUND OF THE INVENTION

This invention relates to electronic signal conditioning circuitry and, more particularly, to circuitry adapted for level adjustment in aperiodic biological signals.

Biological and physiological phenomena are often examined by electronic apparatus. A common example of such apparatus is found in electrocardiology wherein electric wires are attached via terminals to selected sites on a person's chest. These wires couple faint electronic signals given off by pulsations of the heart muscle to signal processing and display equipment which produce graphical recordings of the waveforms of the electronic signals given off by the heart, such recordings being known as electrocardiograms. The various wires provide differing signal waveforms depending on the sites of their respective terminals. Further examples in the measurement of biological waveforms are found in encephalograms and in the study of speech. In each case, electrodes are attached to the subject to obtain the various signals for analysis of their respective waveforms.

As an example of the types of electronic equipment utilized in the measurement and analysis of biological signals, U.S. Pat. No. 3,602,706 of J. R. Levitt discloses a system useful for cardiograms and comprising a set of integrators arranged in feed-forward configuration and providing, in conjunction with a sine function computer, nonlinear transformations for visualization of heart function. An earlier embodiment of such a system, employing simpler circuitry, is shown in the U.S. Pat. 3,422,264 of J. R. Levitt.

Signal processors utilized in the analysis of biological signals, as well as signals obtained from other sources, may be fabricated of analog or digital circuitry. Today, it is usually the practice for such signal processors to employ digital circuits to take advantage of digital signal processing techniques. The biological signals sensed at the electrodes are in analog form. Accordingly, the digital signal processors employ analog to digital convertors for converting the format of the signals from digital to analog form. In a processor capable of high resolution of the signal waveforms, the A/D converters have many stages to provide the many bits of resolution as are required.

A problem arises in that the information contained in the sensed biological signals resides in only a fraction of the amplitude excursion. Typically, the signal is composed of a time-varying component superposed on a constant, or dc (direct current) level, component. In addition, the dc level may drift in amplitude at a rate which is slow compared to the rate of change in the time-varying component. Such drifting does not contain useful information and, accordingly, is to be deleted in the signal processing operation. The foregoing problem is also manifested in the need for analog to digital conversion which can extend over a wide range of values to accomodate the sum of both the varying component and the fixed component. This results in the need for far more extensive conversion equipment or, alternatively, a relaxation in the requirement for the number of bits of amplitude resolution to be used in the signal processing. In either case, the cost of the equipment is greater than desired for the amount of benefit received.

SUMMARY OF THE INVENTION

The foregoing problem is overcome and other advantages are provided by processor of biological signals which, in accordance with the invention, includes a signal conditioner connected between the input signal terminals and the digital circuitry of the signal processor to reset the dc level and suitably scale the amplitude range of the time-varying component so as to render the signal amenable to digital signal processing. It is an object of the invention to provide a signal conditioner operative upon an analog biological signal to reform the signal into a format which is free of dc-level drift and is suitably scaled for use with digital signal processing equipment.

In accordance with the invention, the signal conditioner operates on a signal having only positive values of voltage. The conditioner comprises a baseline shifting unit which removes a sufficient amount of dc level so as to bring the portions of the waveform having the lowest voltage down to zero volts. Thus, the output of the conditioner shifting unit remains in the format of a non-return-to-zero (NRZ) waveform. The ouput signal of the conditioner is free of negative voltage so that an A/D converter of the conditioner need not process negative values of voltage, this simplifying the electrical circuitry. The shifting unit is responsive to timing signals provided by an internal timing unit or an external computer to sample and analyze selected intervals of the biological signal waveform.

The conditioner further comprises a feedback circuit which compares the peak output voltage of the conditioner with a selected reference value, and, in accordance with the comparison, adjusts the gain of the conditioner to attain the desired output voltage range. Included in the conditioner is a gain control circuit comprising a variable gain amplifier and an integration unit which derives the gain control of the amplifier in accordance with the foregoing comparison. The integration is accomplished digitally by a counter and a source of clock pulses wherein the clock pulses are coupled via a logic circuit to the counter in accordance with commands of a comparator providing the foregoing comparison. An offset circuit is also provided at the output of the amplifier so as to accommodate a display device or other signal processor requiring a specific value of offset voltage.

The foregoing circuitry operates in conjunction with a waveform analyzer which measures the elapsed time between heartbeats, and resets the integrator and the shifting unit upon the occurrence of an excessive irregularity in the heartbeat.

BRIEF DESCRIPTION OF THE DRAWING

The foregoing aspects and other features of the invention are explained in the following description, taken in connection with the accompanying drawing wherein.

DETAILED DESCRIPTION

Figure 1:
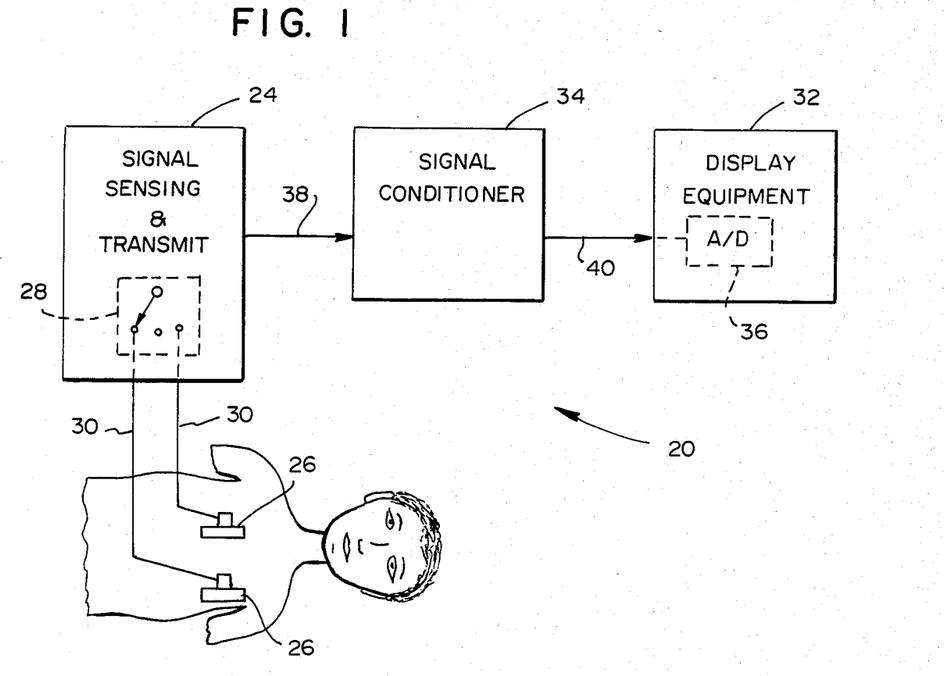
FIG. 1 is block diagram of an electro-cardiogram system incorporanting a signal conditioner of the invention.

With reference to FIG. 1, there is shown a system 20 for producing cardiograms of a patient 22. The system 20 comprises a sensing unit 24 which includes electrodes 26 connected to the patient 22 and a switch 28 for selecting which electrode is to be employed for the cardiogram. Preferably, fiber optic lines 30 are utilized for coupling heart-beat signals to the selector switch 28 in which case the sensing unit 24 includes well-known circuitry (not shown) for converting between optical and electronic signals. The signals are presented in the format of a cardiogram on a display unit 32 which employs conventional signal processing circuitry to show the cardiogram.

The signal processing is enhanced in accordance with the invention by a signal conditioner 34 which couples signals between the sensing unit 24 and the display unit 32. First, it is noted that the signal provided by the sensing units 24 is to be altered by the conditioner 34 for effective processing by the display unit 32. Such alteration is to free the signal from the drift of a baseline, to remove the baseline because the baseline contains no useful information, to adjust the gain of the signal so as to make full use of the range of any analog-to-digital conversion equipment 36 which may be present in the display unit 32, and to introduce a fixed voltage offset which may be required for positioning the signal within the optimum processing range of the display unit 32. Typically, the conversion of optical signals of the lines 30 to electrical signals introduces a relatively fixed positive voltage offset which is larger than negative excursions in the signal wave form. This results in an overly large range of voltage which must be processed prior to the displaying of the electrocardiogram. In addition, the offset tends to drift and, thus, would introduce an error if not compensated.

Secondly, it is noted that not all heart-beat wave forms are to be displayed. For example, fibrillation is not to be displayed. Only substantially regular wave forms within the normal range are to be displayed. Accordingly, the signal conditioner 34 measures the time duration of the intervals between successive heartbeats, and outputs data only during a normal range of heart-beat frequencies.

Figure 2:
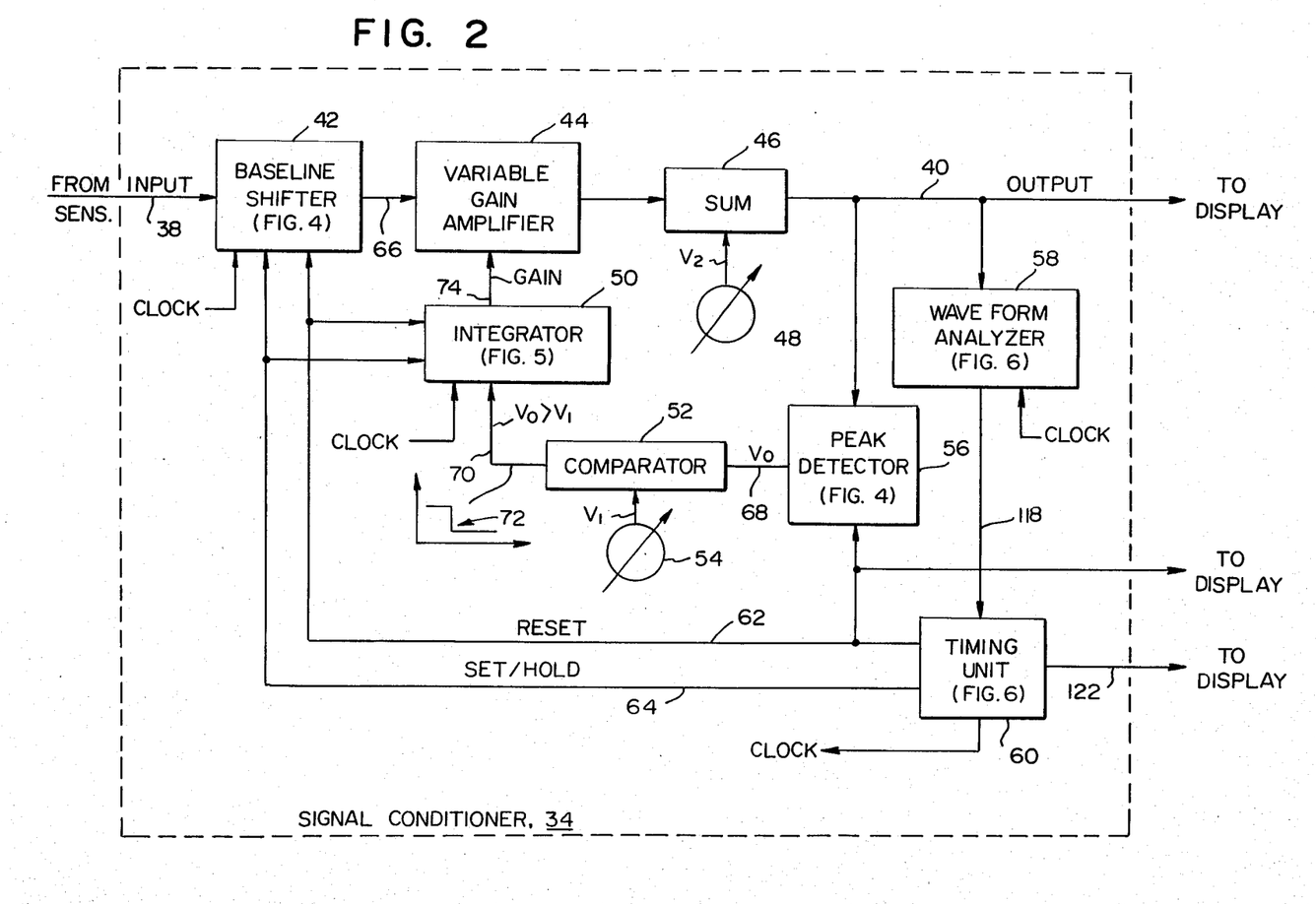
FIG. 2 is a block diagram of the signal conditioner of FIG. 1.
Figure 3:
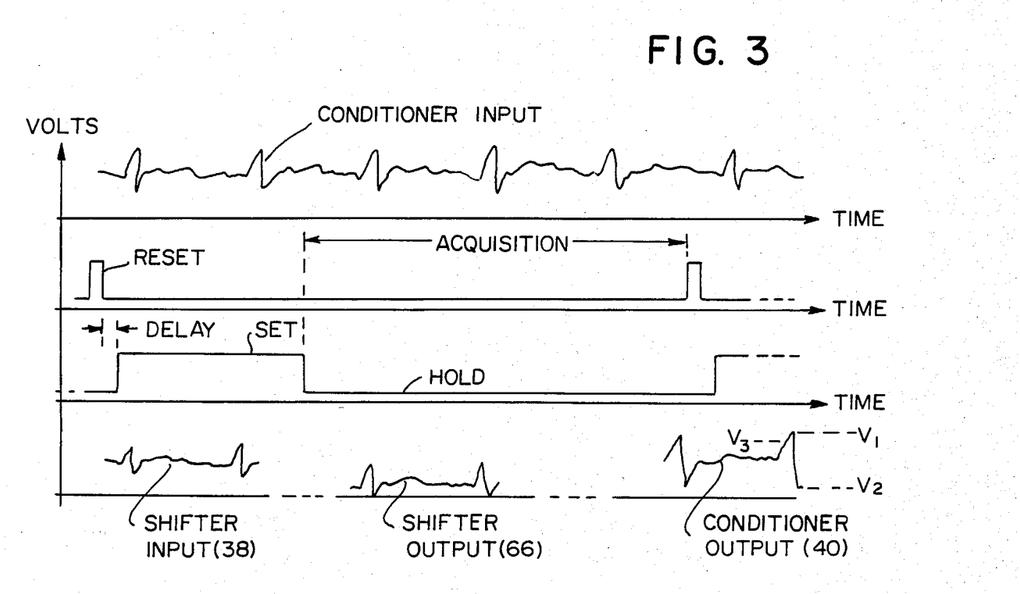
FIG. 3 is a set of graphs showing timing diagrams useful in explaining the operation of the conditioner of FIG. 2.

With reference also to FIGS. 2 and 3, the signal conditioner 34 receives an input signal on line 38 from the sensing unit 24, and provides an output signal on line 40 to the display unit 32. The conditioner 34 comprises a baseline shifter 42, a variable-gain amplifier 44, a summer 46, an adjustable source 48 of a reference signal for the summer 46, an integrator 50, a corparator 52, an adjustable source 54 of a reference signal for the comparator 52, a peak detector 56, a waveform analyzer 58, and a timing unit 60. The input signal on line 38 is depicted in the first graph of FIG. 3. A reset signal is provided by the timing unit 60 on line 62 and is depicted in the second graph of FIG. 3. The timing unit 60 provides a set signal on line 64 which is depicted in the third graph of FIG. 3 and, as will be described subsequently serves to hold the shifter 42 during a specific state of operation for the acquisition of data to be presented on the display unit 32. The first three graphs of FIG. 3 are in time registration with each other so as to show the temporal relationship among the signals shown therein. The fourth graph of FIG. 3 depicts the alteration in baseline produced by the shifter 42, as well as a shift in both baseline and amplitude produced by the amplifier 44 and the summer 46 and appearing at the output terminal of the conditioner 34.

In operation, the shifter 42 reduces the baseline voltage so that the lower excursions of the input signal waveform are at zero volts, this being attained at the output terminal of the shifter 42 on line 66. The shift in baseline is presented in the first two waveforms in the fourth graph of FIG. 3. Thereupon, the shifter output signal on line 66 is scaled by the amplifier 44 and offset by the summer 46 by a voltage V2 from the level appearing on line 66. Thus, the output signal on line 40, as depicted in the third waveform of the fourth graph of FIG. 3, ranges from a minimum value of V2 to a maximum value of V1. The offset voltage V2 is produced by the source 48 and summed with the output signal of the amplifier 44 by the summer 46. The value of V2 may be set to any desired positive value ranging from zero volts to a value convenient for use in the display unit 32.

The maximum value, V1, is introduced by the source 54 and may be adjusted to any desired value by the use of the source 54. The peak value of the voltage on line 40 is sensed by the detector 56 and provided on line 68 as V0. The comparator 52 is coupled to the source 54 and to the detector 56 for comparing the two voltages V1 and V0. The resulting output signal of the comparator 52, on line 70 is depicted in a graph 72 shown in FIG. 2 adjacent the line 70. The output signal of the comparator 52 indicates whether the maximum output voltage of the conditioner 34, V0, is greater than or less than the desired peak value, V1. The gain of the amplifier 44 is controlled by a signal provided by the integrator 50. The comparator signal on line 70 strobes the integrator 50 to vary the gain of the amplifier 44, in a manner to be described subsequently, so as to attain equality between V0 and V1.

In response to the reset signal on line 62, the integrator 50 introduces a maximum value of gain to the amplifier 44 resulting in a maximum output voltage, V0, which is substantially greater than the desired value V1. Thereafter, during the duration of the set pulse signal on line 64, the integrator 50 decreases the value of the gain control signal on line 74 until the desired equality of V0 and V1 is attained.

The duration of the reset pulse (depicted in FIG. 3) is long enough to discharge a clamping capacitor utilized in the peak detector 56 and another such detector utilized in the shifter 42 as will be described with reference to FIG. 4. Typically, a reset pulse duration of 10 milliseconds is sufficient. The duration of the set signal is long enough for observation of at least one complete interval between successive heartbeats; an interval of 1.5 seconds is sufficient for the lowest anticipated heartbeat frequency of 40 beats per minute. The delay between the reset and the set pulses, as shown in FIG. 3, is approximately 10 milliseconds to allow for the settling of any transients associated with the resetting process prior to the introduction of the set pulse. The duration of an aquisition interval, between the terminus of the set pulse and the inception of the next reset pulse is sufficiently long for the observation of a few intervals of the heart-beat waveform. In the case of the resting cardiogram, an aquisition time of approximately 4 seconds allows for the viewing of a few intervals of the heartbeat waveform with no more than a negligible drift in the baseline. Thereafter, the shifter 42 is reset and, during the subsequent set interval, re-establishes the appropriate baseline compensation so as to insure that the baseline drift has been properly compensated for the subsequent acquisition interval. Thereby, any drift in the baseline is compensated repetitively so as to insure that the cardiogram data acquired during the successsive acquisition intervals can be viewed without any noticeable error due to baseline drift.

In order to insure that the cardiogram presented by the display unit 32 is based on data associated with a normal heartbeat waveform, so as to eliminate effects of fibrillation and other anomalies, the analyzer 58 analyzes the output waveform of the conditioner 34, in a manner to be described subsequently with reference to FIG. 6, so as to restart the timing unit 60 and reset the conditioner 34 upon the occurrence of an anomalous waveform. Thereby, the shifter 42 and the integrator 50 are operated during a further set pulse so as to reintroduce an acquisition interval subsequent to the anomalous waveform.

Figure 4:
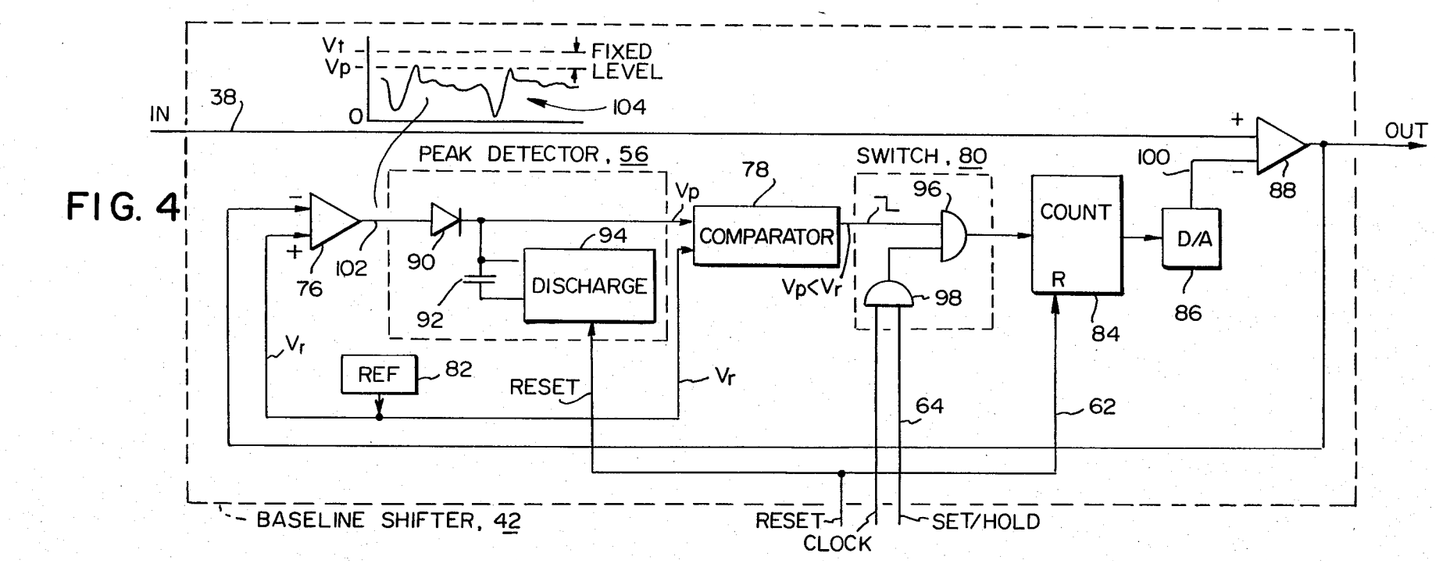
FIG. 4 is a baseline shifter in the conditioner of FIG. 2.

With reference to FIG. 4, the baseline shifter 42 comprises a differential amplifier 76, a peak detector 56 of the same form as that disclosed in FIG. 2, a comparator 78, an electronic switch 80, a source 82 of a reference voltage for use by the amplifier 76 and the comparator 78, a counter 84, a digital-to-analog converter 86 and a differential amplifier 88. The peak detector 56 comprises a diode 90, a capacitor 92 which is charged via the diode 90, and a discharge circuit 94 of conventional design for discharging the capacitor 94 upon receipt of the reset signal. The electronic switch 80 comprises a first AND gate 96 coupling the comparator 78 to the counter 84, and a second AND gate 98 having an output terminal connected to an input terminal of the gate 96. The shifter 42 operates in response to the reset signal on line 62 and the set signal on line 64, as shown in FIG. 2, and is also responsive to clock pulse signals provided by the timing unit 60 of FIG. 2.

In operation, the amplifier 88 provides a summing function for combining the input signal on line 38 with a feedback signal on line 100 to produce the output signal on line 66. The feedback signal on line 100 is subtracted from the input signal on line 38 so as to reduce the amount of offset associated with the baseline. The output signal on line 66 is compared with the fixed value of the reference signal from the source 82 by the amplifier 76, the amplifier 76 subtracting the two signals from each other so as to produce a difference signal on line 102 at the output terminal of the amplifier 76. The difference signal on line 102 is portrayed in a graph 104 located adjacent the line 102.

As shown in the graph 104, the waveform of the signal on line 102 is inverted from that on line 38, shown in FIG. 3. The inversion is due to the subtraction of the signal on line 66 from the fixed value of the reference signal from the source 82. Thus, the negative excursion of the signal on line 38 becomes the positive excursion of the signal on line 102. The reference signal of the source 82 is identified as the Vr. The maximum excursion, or peak value, of the waveform in the graph 104 is identified as Vp. The magnitude of Vr is chosen to be larger than the maximum value of the signal on line 38 so that, upon inversion of the signal waveform, all of the waveform has positive values of voltage.

The detector 56 detects the peak value of the signal on line 102 and applies the peak value, Vp, to an input terminal of the comparator 78. The comparator 78 compares Vp with Vr to provide a binary signal(having a logic level of 1 or 0) to an input terminal of the gate 96. The peak detector 56 operates in a well-known manner whereby a signal current on line 102 passes through the diode 90 to charge the capacitor 92 to a voltage equal to the peak. This voltage is then retained by the capacitor 92 during subsequent undulations in the amplitude of the signal on line 102. The discharge circuit 94, which may comprise a well-known transistor circuit connected across the terminals of the capacitor 92, is activated by the reset pulse for discharging the capacitor during the resetting of the conditioner 34 as has been described previously with reference to FIGS. 2 and 3. For example, the reset pulse might be applied to a base terminal of the foregoing transistor (not shown) for drawing current and stored charge from the capacitor 92.

The binary signal from the comparator 78 activates the gate 96 to couple clock pulse signals to the counter 84. The counter 84 counts the clock pulses and outputs the resulting count to the converter 86. The converter 86 converts the digital number to an analog signal which signal is the aforementioned feedback signal on line 100.

The gates 96 and 98 of the switch 80 serves to switch on the flow of clock pulses to the counter 84 only during the presence of the set pulse on line 64, and only during such time as the comparator 78 is outputting a logic-1 signal indicating that Vp is greater than Vr. As a result, the feedback signal on line 100 is understood to increase in value, in the form of a ramp waveform, until such time as Vp is equal to Vr. Thereupon, the comparator 78 shuts down the switch 80 and the counter 84 retains its final count. Thereupon, the feedback signal on line 100 remains constant.

With reference also to the timing diagrams of FIG. 3, both the discharge circuit 94 and the counter 84 are reset by the reset signal. Thereafter, during the duration of the set pulse, the counter 84 operates to shift the baseline by the requisite amount. At the conclusion of the set pulse, the set signal reverts from a logic-1 to a logic-0, the logic-0 state being designated as a hold interval in the third graph of FIG. 3. During the hold interval, the switch 80 decouples the clock pulses from the counter 84 so that the counter 84 remains constant and, correspondingly, the analog signal provided by the converter 86 on line 100 is also constant until the occurrence of the next reset pulse which resets the counter 84 to zero. Also, during the duration of the set pulse, the peak detector 56 samples the difference signal on line 102 so as to provide a value of Vp corresponding to the maximum excursion of the waveform depicted in the graph 104. A new measurement of the maximum voltage, Vp, is enabled by the discharging of the capacitor 92 in response to the current of the reset pulse prior to the set pulse.

Figure 5:
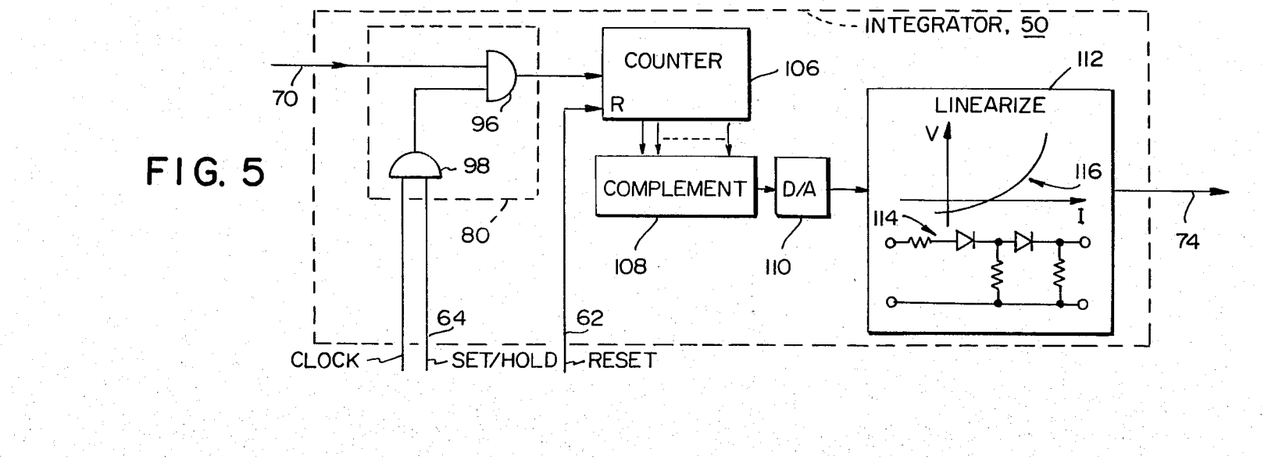
FIG. 5 is a block diagram of an integrator in the conditioner of FIG. 2.

In FIG. 5, the integrator 50 is shown to comprise a switch 80, a counter 106 with a complementing unit 108 coupled to the output terminals of the counter 106, a digital-to-analog converter 110 and a linearizing unit 112. The interconnection of the integrator 50 with other components of the conditioner 34 has been disclosed in FIG. 2 wherein the input signal is applied along line 70 from the comparator 52, and the output signal of the integrator 50 is coupled via line 74 to the amplifier 44. The switch 80 in the integrator 50 comprises the same components as does the switch 80 in the shifter 42 of FIG. 4 and, in addition, includes the clock signal, the set signal, and the reset signal disclosed in FIGS. 2 and 4. Thus, the operation of the switch 80 in the integrator 50 is the same as that of the switch 80 in the shifter 42. Also, it is noted that the operation of the peak detector 56 and the comparator 52 of FIG. 2 for providing a signal along line 70 to the switch 80 corresponds to the operation of the peak detector 56 and the comparator 78 of FIG. 4 in applying a signal to the switch 80 of FIG. 4.

In operation, the counter 106 counts clock pulses during the duration of the set pulse on line 64, and for such time as the voltage V0 (FIG. 2) is greater than the voltage V1(FIG. 2). By virtue of the complementing unit 108, the counter 106 is converted to a down counter with the result that the count applied by the complementing unit 108 to the converter 110 decreases with increasing counting of clock pulses. The converter 110 converts the count to an analog voltage which is applied via the linearizing unit 112 to the amplifier 44(FIG. 2). Thereby, with increased counting of clock pulses, the voltage on line 74 is reduced to reduce the gain of the amplifier 44. As is well known, the amplifier gain versus control voltage is a non-linear relationship and, accordingly, the linearizing unit 112 is utilized for compensating the non-linear characteristic to produce a substantially linear relationship. As is well known, such a compensating relationship may be attained with a diode-resistor circuit such as that suggested at 114. A stylized representation of the voltage-current relationship for such a non-linear circuit is shown in the graph 116 presented along with the circuit 114 in the block designating the linearizing unit 112.

In view of the foregoing description, it is evident that both the baseline shifter 42 and the integrator 50 are reset by the reset pulse and then activated during the duration of the set pulse to introduce the requisite baseline shifting and the requisite scaling of the input signal on line 38. Thereafter, during the hold interval and up to the occurence of the next reset pulse, the counts of both the counter 106 (FIG. 5) and 84 (FIG. 4) remain constant. They are reset to zero by the following reset pulse on line 62. Thereby, the signal conditioner 34 is reactivated prior to each acquisition interval to insure that the drift has been compensated and that the output signal of the conditioner 34 extends through the full range from V2 to V1.

Figure 6:
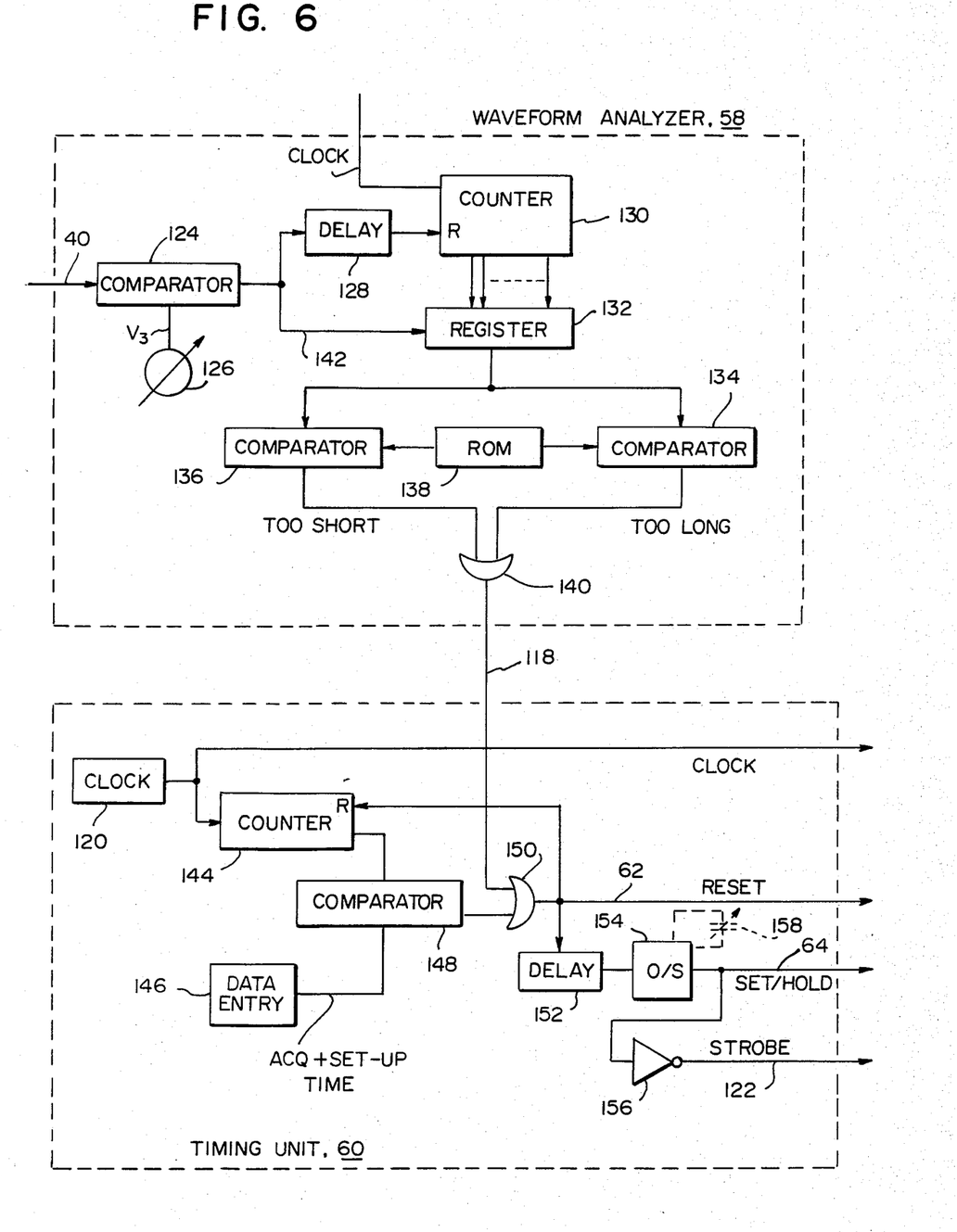
FIG. 6 is a block diagram of a waveform analyzer and a timing unit of the conditioner of FIG. 2.

With reference now to FIG. 6, there is shown the construction of the waveform analyzer 58 and the timing unit 60 which were previously described in FIG. 2. The analyzer 58 receives its input signal on line 40 and outputs a signal on line 118 to the timing unit 60. The timing unit 60 includes a clock 120 which provides clock pulse signals to the analyzer 58 as well as to the other components as disclosed previously with reference to FIG. 2. The timing unit 60 also includes circuitry, to be described presently, which produces the reset signal, the set signal, as well as a strobe signal on line 122. Both the reset signal and the strobe signal are applied to the display unit 32 along with the output signal of the conditioner 34 on line 40.

The analyzer 58 comprises a comparator 124, a variable voltage source 126 for providing a reference voltage V3 to the comparator 124, a delay unit 128, a counter 130, a register 132, two comparators 134 and 136 which are connected to a common output port of the register 132, a ROM 138 (read-only memory) which provides reference signals to each of the comparators 134 and 136, and an OR gate 140.

In operation, the comparator 124 is used for identifying the presence of a heartbeat in the waveform of the signal on line 40. By setting the value of the reference voltage V3 to a value somewhat less than that of V1 (FIG. 3), the comparator 124 outputs a logic-1 signal on line 142 upon the presence of the peak of the signal waveform, but not otherwise. The pulse signal on line 142 strobes the register 132 to read the count of the counter 130, and then, after a momentary delay provided by the delay unit 128, resets the counter 130. The counter 130 counts clock pulses produced by the clock 120. The counter 130 counts continuously until such times as it is reset by the comparator signal on line 142. Thus, there appears a sequence of counts in the register 132, each of which represents the duration of an interpulse interval between two successive heartbeats in the output signal waveform on line 40 of the conditioner 34. The counts stored in the register 132 are outputted to the comparators 134 and 136 which compare the measured interpulse intervals with reference intervals stored in the memory 138. The reference signal outputted by the memory 138 to the comparator 134 is the maximum length of acceptable interpulse interval. The reference interval outputted by the memory 138 to the comparator 136 is the minimum length of an acceptable interpulse interval. Accordingly, the comparator 134 outputs a signal to the gate 140 in the event that the measured interval is too long, and the comparator 136 outputs a signal to the gate 140 in the event that the measured interval is too short. The gate 140 couples the output signals of the comparators 134 and 136 to the timing unit 60 via the line 118, the signals on the line 118 being used to restart the timing unit 60. The presence of either signal on line 118 indicates that the interpulse interval is of an unacceptable duration and, accordingly, the conditioner 34 should be reset and a new aquisition interval established.

The timing unit 60 comprises a counter 144, a source 146 of data entry such as a keyboard or similar device, a comparator 148, an or gate 150, a delay unit 152, a monostable multivibrator or one-shot 154, and a digital inverter 156. Both the delay units 128 and 152 may be fabricated as monostable multivibrators or comparable well-known circuitry.

In operation the counter 144 counts clock pulses provided by the clock 120. A person operating the system 20 (FIG. 1) enters the length of the acquisition time at the data-entry source 146. The comparator 148 compares the count of the counter 144 with the length of the aquisition time provided by the source 146. The comparator 148 outputs a pulse to the gate 150 when the magnitude of the count 144 reaches the desired length of the aquisition interval. The output signal of the gate 150 is the aforementioned reset signal on line 62. The reset signal is coupled to the reset terminal (R) of the counter 144 for resetting the count thereof back to zero. Thus, the counter 144 counts out the duration of the time interval between successive reset pulses, this being equal to the sum of the aquisition time plus the set-up time associated with the functions occuring during the reset and set pulses. Accordingly, in entering the data at the source 146, the operator enters the total of the aquisition plus the set up times.

The reset pulse on line 62 is also applied via the delay unit 152 to the multivibrator 154, the output of which is the set signal on line 64. Thus, the multivibrator 154 produces a logic-1 signal during the duration of the set pulse and a logic-0 signal during the hold interval between successive ones of the set pulses. The delay introduced by the delay unit 152 is the delay depicted in FIG. 3 between the reset and the set pulses. The output signal of the multivibrator 154 is also applied to the inverter 156 to produce the strobe signal on line 122. Thus, it is seen that the strobe signal contains a logic-1 value and, accordingly, enables the display unit 32 to present the cardiogram data until reception of the next reset signal from the signal conditioner 34.

It is noted that the reset signal can be produced by either the output pulse of the comparator 148 or, alternatively, either of the output pulses of the comparators 134 and 136 the latter being coupled to the reset line 62 by the gates 140 and 150. Thereby, upon the recognition of an unacceptable duration of interpulse interval by the analyzer 58, the timing unit 60 is reset by the signal on line 118 and the counter 144 is restarted to provide for a new aquisition and set-up time.

In view of the foregoing description, there is provided a signal conditioner which effectively compensates for baseline drift in heart-beat signal data provided by sensing units such as the sensing unit 24 of FIG. 1. In addition, the signal conditioner provides for an updating of the scaling and any desired offset voltage as may be required by a display unit for the displaying of cardiographic data. Such updating is provided periodically between each of a succession of aquisition intervals during which the data is presented to the display. It is also noted that the foregoing description, while being directed to the waveforms associated with cardiographic data, can also be utilized for other waveforms characterized by a succession of peaks separated by relatively low values of signal amplitude such other waveforms being obtained during observation of other biological phenomenon such as speech and other electrical signal associated with living organisms. For use with some other form of biological signal, such as speech, the duration of the set pulse would be adjusted, as by use of an external variable capacitor 158 connected to the multivibrator 154 for adjusting the duration of the set pulse to cover a sufficient interval of the speech for observation of the maximum values thereof. It is also noted that the circuitry of the conditioner 34 provides for stable operation during the duration of the set pulse since the counter 106 (FIG. 5) and the counter 84 (FIG. 4) serve as integrators by virtue of the counting of the clock pulses. These integration functions permit the circuitry to precisely attain the desired values of baseline shift and signal scaling.

Figure 7:
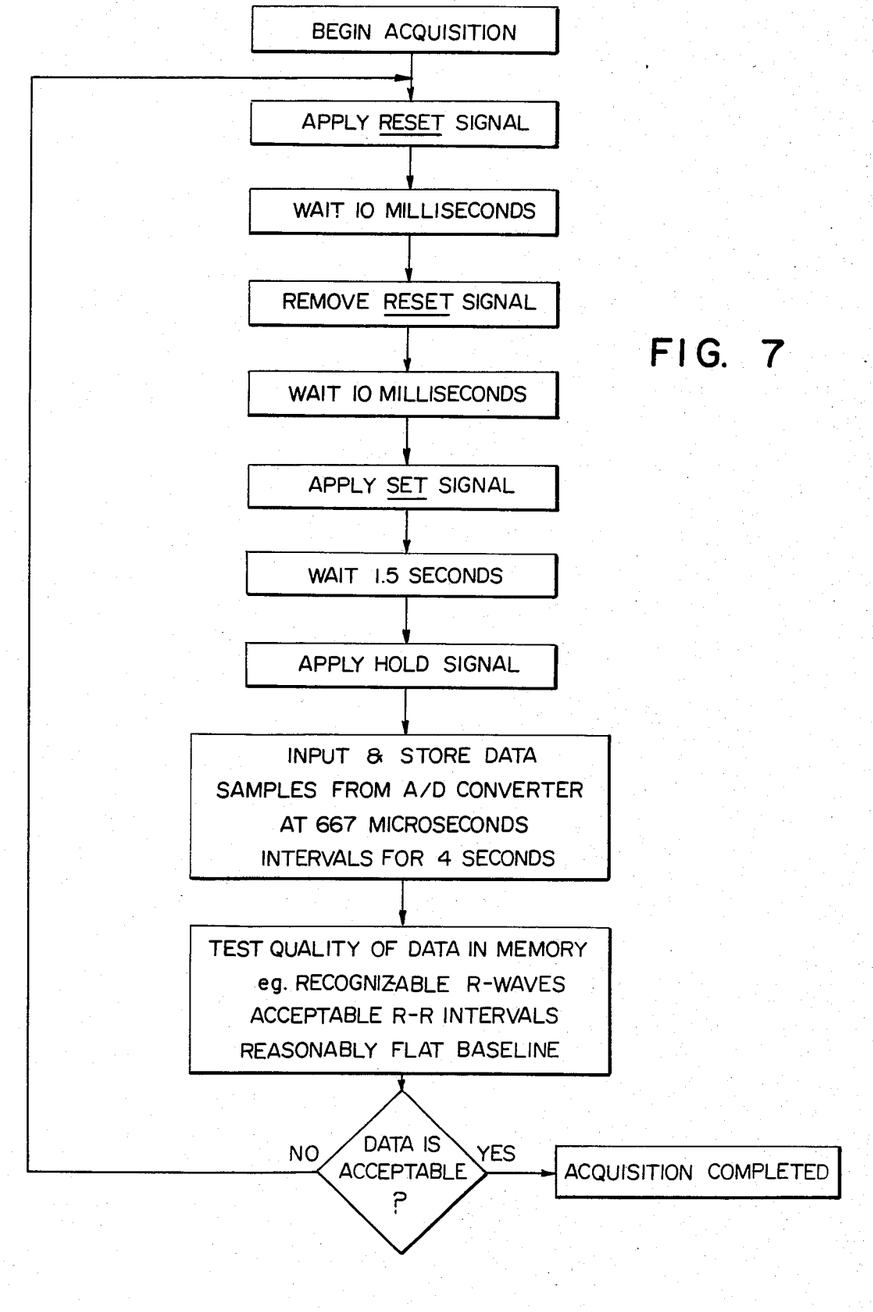
FIG. 7 is a flow chart showing a sequence of steps in the operation of the signal conditioner.

It is also noted, by way of alternative embodiments, that the circuitry included within the timing unit 60 (FIG. 6) may also be included within a computer such as might be utilized in a data processor for the processing and display of cardiographic data. In the event that such external computation apparatus be employed, the clock, reset and set signals can be developed by the data processing equipment for synchronizing the operation of the signal conditioner to the operation of the data processor. The sequence of operations of the signal conditioner, as would be set forth in the program of such a data processor, would follow the flow chart as set forth in FIG. 7. The order of operation steps set forth in FIG. 7 follows that taught in the preceding description of the signal conditioner 34. It is further noted that, in the event that an external data processor is employed, some sort of waveform analysis may also be performed corresponding to that disclosed above with reference to the analyzer 58. Such analysis is referred to in the chart of FIG. 7 wherein one of the steps relates to the testing of the data quality.

It is to be understood that the above described embodiments of the invention are illustrative only, and that modifications thereof may occur to those skilled in the art. Accordingly, this invention is not to be regarded as limited to the embodiments disclosed herein, but is to be limited as defined by the appended claims.

What is claimed is:

1. A signal conditioner suitable for conditioning an input signal composed of a time-varying component superposed on a fixed component subject to amplitude drift, the conditioner having an input terminal and an output terminal further comprising:

a baseline shifting unit coupled to said input terminal of said conditioner, said shifting unit including means for adjusting the minimum amplitude of the input signal relative to a baseline;

a variable gain amplifier coupled to an output terminal of said shifting unit, said variable gain amplifier including means for adjusting the maximum amplitude of the input signal relative to the baseline;

a source of reference signal for establishing the maximum amplitude of the input signal;

comparator means coupled between said reference source and said output terminal of said conditioner for providing a feedback signal;

means for providing a clock pulse signal;

integration means responsive to the clock pulse signal and activated by the feedback signal for providing a gain control signal to said amplifier; and timing means coupled to said shifting unit and to said integration means for setting and resetting said shifting unit and said integration means, said shifting unit and said integrating means including resettable means for providing an output signal having a magnitude dependent on the number of clock pulses in a sequence of said clock pulses, said shifting unit and said integrating means further comprising switching means responsive to a set timing signal for gating a sequence of the clock pulses to said resettable means, and said amplifier scaling the input signal subsequent to alteration of its baseline by said shifting unit.

2. A conditioner according to claim 1 wherein, in said shifting unit, said resettable means is an integrator and said shifting unit further comprises:

a summer connected between an input terminal and an output terminal of said shifting unit, a first input terminal of said summer being connected to the input terminal of said shifting unit;

a feedback amplifier serially connected with said integrator via said switching means in a feedback path between a second input terminal and an output terminal of said summer; and wherein said switching means is operative in response to signals of said timing means for switchably coupling said integrator to said means for providing clock pulses for integrating the time of a sample interval of said input signal, the length of the sample interval being established by said sequence of clock pulses.

3. A conditioner according to claim 1 wherein, in said integration means said resettable means is a counter which counts clock pulses, said integration means further comprises:
a digital-to-analog converter which is coupled to said counter for converting its output count to an analog voltage to serve as said gain control signal; and wherein said switching means is responsive to the feedback signal of said comparator means for gating individual ones of the clock pulses to said counter, thereby altering the gain of said variable-gain amplifier to attain a desired amplitude to an output signal of said conditioner.

4. A conditioner according to claim 3 further comprising means coupled between said variable-gain amplifier and the output terminal of said conditioner for offsetting the voltage of the output signal of said conditioner by a predetermined amount.

5. A conditioner according to claim 4 wherein said clock pulse providing means comprises a clock which provides said clock pulses, and wherein in said shifting unit, said resettable means is an integrator and said shifting unit further comprises:
a summer connected between an input terminal and an output terminal of said shifting unit, a first input terminal of said summer being connected to the input terminal of said shifting unit;
a feedback amplifier serially connected with said integrator via said switching means in a feedback path between a second input terminal and an output terminal of said summer; and wherein
said switching means is operative in response to signals of said timing means for switchably coupling said integrator to said feedback amplifier for integrating clock pulse signals over predetermined intervals of said input signal.

6. A conditioner according to claim 5, wherein said timing means is resettable and includes resettable counting means responsive to said clock pulse signal for designating an interval of time; said conditioner further comprising analyzer means responsive to the waveform of an output signal of said conditioner for resetting said timing means, said integration means, and said shifting unit when said waveform has a characteristic lying outside the normal range of such characteristic.

7. A conditioner according to claim 6 wherein said analyzer means comprises means for sensing a peak of said waveform, means coupled to said peak sensing means for measuring the interval between successive peaks of said waveform, and means for comparing the interval between said peaks with reference values of such intervals to determine if the interval is in said normal range.

8. A conditioner according to claim 1 further comprising analyzer means reponsive to the waveform of an output signal of said conditioner for resetting said timing means, said integration means and said shifting unit when said waveform has a characteristic lying outside the normal range of such characteristic.

9. A conditioner according to claim 8 wherein said analyzer means comprises means for sensing a peak of said waveform, means coupled to said peak sensing means for measuring the interval between successive peaks of said waveform, and means for comparing the interval between said peaks with reference values of such intervals to determine if the interval is in said normal range.

10. A signal conditioner suitable for conditioning an input signal composed of a time-varying component superposed on a fixed component subject to amplitude drift, the conditioner comprising:
a baseline shifting unit coupled to an input terminal of said conditioner;
timing means coupled to said shifting unit for setting and resetting said shifting unit; and
analyzer means responsive to the waveform of an output signal at an output terminal of said conditioner for resetting said timing means and said shifting unit when said waveform has a characteristic lying outside the normal range of such characteristic, said timing means including means for measuring elapsed time between successive pulsations of said time varying component of said input signal to obtain said characteristic of said waveform.

11. A conditioner according to claim 10 wherein said shifting unit comprises:
a summer connected between an input terminal and an output terminal of said shifting unit, a first input terminal of said summer being connected to the input terminal of said shifting unit;
switching means;
a feedback amplifier and an integrator serially connected via said switching means in a feedback path between a second input terminal and an output terminal of said summer, said timing means including a source of clock pulses, and means for designating a sampling interval of the input signal to said conditioner; and wherein
said switching means is operative in response to signals of said timing means for switchably coupling said integrator to said source of clock pulses for integrating the time of a sample interval of said input signal.

12. A conditioner according to claim 11 wherein said analyzer means comprises means for sensing a peak of said waveform, said elapsed time means being coupled to said peak sensing means for measuring the interval between successive peaks of said waveform, and means for comparing the interval between said peaks with reference values of such intervals to determine if the interval is in said normal range.

13. A conditioner according to claim 12 wherein said integrator is a counter of said clock pulses.

14. A conditioner according to claim 13 further comprising:
a variable gain amplifier coupled to said output terminal of said shifting unit;
comparator means coupled to said output terminal of said conditioner for providing a feedback signal;
a second counter responsive to a clock pulse signal of said clock-pulse source and activated by the feedback signal of said comparator means for providing a gain control signal to said amplifier;
a digital-to-analog converter which is coupled to said second counter for converting its output count to an analog voltage to serve as said gain control signal; and
means responsive to the feedback signal of said comparator means for gating individual ones of the clock pulses to said second counter, thereby altering the gain of said variable-gain amplifier to attain a desired amplitude to an output signal of said conditioner.

15. A conditioner according to claim 14 wherein said second counter counts down for reducing a gain of said variable gain amplifier to produce a desired output voltage level at the output terminal of said conditioner.

* * * * *